United States Patent [19]

Nakagawa et al.

[11] 4,211,785

[45] Jul. 8, 1980

[54] FUNGICIDAL COMPOSITION FOR USE IN AGRICULTURE AND HORTICULTURE AND ITS USE

[75] Inventors: Taizo Nakagawa, Ageo; Yutaka Watanabe, Saitama; Kaoru Ohmori, Okegawa, all of Japan

[73] Assignee: Nippon Kayaku Kabushiki Kaisha, Tokyo, Japan

[21] Appl. No.: 893

[22] Filed: Jan. 4, 1979

[30] Foreign Application Priority Data

Jan. 19, 1978 [JP] Japan .................................. 53-3737

[51] Int. Cl.$^2$ .............................................. A01N 9/02
[52] U.S. Cl. ...................................... 424/272; 424/300
[58] Field of Search .................. 260/456 A; 424/272, 424/300

[56] References Cited

U.S. PATENT DOCUMENTS 3,544,584  12/1970  Iwai et al. ............................ 424/272

OTHER PUBLICATIONS

Chemical Abstracts, vol. 84 (1976), p. 70333u.

*Primary Examiner*—V. D. Turner
*Attorney, Agent, or Firm*—Stevens, Davis, Miller & Mosher

[57] ABSTRACT

A fungicidal composition useful in agriculture and horticulture comprising as effective components 4-methylsulfonyl-oxyphenyl-N-methylthiolcarbamate and 3-hydroxy-5-methylisoxazol. These effective components are generally mixed with at least one adjuvant when practically applied. A method for controlling soil borne plant diseases is also described using the fungicidal composition.

5 Claims, No Drawings

FUNGICIDAL COMPOSITION FOR USE IN AGRICULTURE AND HORTICULTURE AND ITS USE

BACKGROUND OF THE INVENTION

This invention relates to a fungicidal composition for use in agriculture and horticulture and more particularly, to a fungicidal composition comprising at least one adjuvant and an effective amount of effective components comprising 4-methylsulfonyloxyphenyl-N-methylthiolcarbamate

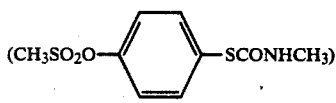

and 3-hydroxy-5-methylisoxazol

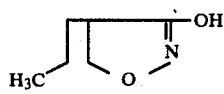

The invention also relates to a method for preventing soil borne plant diseases caused by fungi which comprises treating fungi-containing soil with an effective amount of the above effective components.

4-methylsulfonyloxyphenyl-N-methylthiolcarbamate (hereinafter referred to simply as "compound A") which is employed as one of the effective components of the fungicidal composition according to the invention is a novel compound. This compound shows effect on fungi such as of Fusarium Sp, Pythium Sp, Rhizopus Sp, Phytophthora Sp, Trichoderma Sp and the like but is lower in activity on fungi of Trichoderma Sp.

On the other hand, 3-hydroxy-5-methylisoxazol (hereinafter referred to simply as "hydroxyisoxazol") is a known compound, which is described, for example, in Japanese Patent Publication No. 42-2440.

The hydroxyisoxazol is commercially available and is now applied so as to prevent a damping-off disease of rice or beet plant. This compound shows activity against the fungi of Fusarium Sp and Pythium Sp but shows low activity against the fungi of Phytophthora Sp, Rhizopus Sp and Trichoderma Sp.

SUMMARY OF THE INVENTION

We have made various studies for developing fungicides which can reliably control soil borne plant diseases such as Phytophthora rot of cucumber or damping-off rice plant and, as a result, found that a mixture of the compound A and the hydroxyisoxazol shows an unexpectedly high synergistic effect without giving any Phytotoxity on crops and can prevent various soil borne plants diseases caused by various causal fungi. To a surprise, it has been also found that the mixture shows an excellent control effect on the damping-off disease of rice plant caused by the Trichoderma Sp on which eigher of the compounds does not exhibit any significant control effect when used singly.

Thus, it is an object of the present invention to provide a fungicidal composition for use in agriculture and horticulture which shows an excellent antifungal activity or effect.

It is another object of the present invention to provide a fungicidal composition which is especially effective in controlling soil borne plant diseases.

It is further object of the present invention to provide a method for controlling soil borne plant disease caused by fungi.

Other object of the present invention will become apparent from the following detailed description of the invention.

DETAILED DESCRIPTION OF THE INVENTION

The invention will be described in detail hereinbelow.

The composition according to the invention usually comprises the compound A and the hydroxyisoxazol in a weight ratio of 1:10–10:1, preferably 1:1–6:1. The composition of the invention may be used in various formulations for application as a fungicidal agent for agriculture and horticulture. That is, the mixture of the compound A and the hydroxyisoxazol is generally admixed with at least one adjuvant, the type of which is properly selected depending on the purpose in end use and is used in the form of, for example, an emulsion, wettable powder, dust, granules, micro granules or flowable agent.

In the case, the effective components comprising of the compound A and the hydroxyisoxazol are used in such an amount as employed in usual agricultural or horticultural fungicides and is generally in the range of 0.5–95 wt%, preferably 2–70 wt%, of the composition. Accordingly, the adjuvant is used in an amount of from 99.5 to 5 wt%, preferably, 98–30 wt% of the composition.

Various types of carriers may be used as the adjuvant including solid and liquid carriers. Examples of the solid carrier are clay, kaolin, talc, diatomaceous earth, silica, calcium carbonate and the like. Examples of the liquid carrier are benzene, alcohols, acetone, xylenes, α-, or β-methylnaphthalene, cyclohexane, dimethylformamide, dimethylsulfoxide, animal and plant oils, fatty acids, fatty acid esters and various surface active agents, and the like. Aside from the carriers, any adjuvants generally employed for agricultural chemicals such as, for example, spreader, emulsifier, wetting agent, breaking agent, dispersant and binder may be used to ensure the antifungal effect of the effective components. These adjuvants may be used singly or in combination of two or more.

The composition according to the invention may be used by mixing with other herbicides, insecticides, miticides, agricultural and horticultural fungicides, soil improvers or fertilizers. It is important to note that the composition of the invention is very effective in controlling soil borne diseases of plants or crops such as vegetables, beans, rice plants and beets.

The novel compound A can be prepared by the following procedure.

SYNTHESIS OF COMPOUND A 4.29 g (0.021 moles) of 4-methanesulfonyloxybenzene-ethiol and 1.3 g (0.023 moles) of methyl isocyanate were dissolved in 20 ml of benzene, to which a drop of triethylamine was added, followed by allowing to stand at room temperature for a while.

The reaction solution was concentrated under reduced pressure to obtain crude crystals. The crude crystals were recrystallized from small amount of benzene to give 4.95 g of white crystals of Compound A.

Yield: 90.0%

Melting point: 91°–91.5° C.

Elementary analysis (for $C_9H_{11}NO_4S_2$): Found: C: 41.60% H: 3.87%, N: 5.38%; Calculated C: 41.38% H: 3.86%, N: 5.37%.

Then detailed formulation examples of the present invention are explained hereunder, however, the kind of the aditives and the mixing ratios should not be limited within the range of the examples but can be utilized in wider ranges for practical uses.

In the formulation examples, parts are by weight.

FORMULATION EXAMPLE 1

Dust

Compound A—10 parts
Hydroxyisoxazol—3 parts
Clay—87 parts

The mixture of the above formulation was mixed and powdered to obtain a dust.

FORMULATION EXAMPLE 2

Wettable Powder 10 parts of Compound A and 20 parts of the hydroxyisoxazol were mixed with 65 parts of kaolin, 3 parts of sodium alkylsulfate and 2 parts of sodium polyacrylate and finely powdered to obtain a wettable powder.

FORMULATION EXAMPLE 3

Granulaces 93 parts of silica granules with a size of 16–32 mesh were applied and covered on the surfaces thereof with a mixture of 4 parts of Compound A, 1 parts of hydroxyisoxazol, both of which had been finely powdered, and 1 part of fine powder of synthetic hydrous silicic acid by the use of 1 part of polyethylene glycol 400 as binder to obtain a granule.

FORMULATION EXAMPLE 4

Micro Granules 93 parts of fine particles of feldspar which had been been shifted out to have a size of 65–250 mesh were admixed with 1 part of polyoxyethylene (n=10) nonylphenyl ether, to which were further added in the following order 4 parts of Compound A, 1 part of hydroxyisoxazol and 1 part of fine powder of synthetic hydrous silicic acid, all of which had been previously finely powdered, thereby giving a micro granule.

In the soil treatment, the amount of the composition may vary depending on the weight ratio of the effective components, the manner of application, the type of formulation and the like. In this connection, however, the composition is applied preferably in an amount of 1–8 kg/10a of compound A and 0.4–4 kg/10a of the hydroxyisoxazol and most preferable 2–6 kg/10a of compound A and 0.8–3 kg/10a of hydroxyisoxazol in the case of overall soil treatment, (where, 10a means 10 ares).

Further, when the composition according to the invention is applied, for example, to a nursery box of a size of 60 cm×30 cm×3 cm, it is preferable to use in an amount of 0.5 g–1.5 g of compound A and 0.08–0.6 g of hydroxyisoxazol per box when calculated as the effective components though the amount may vary, more or less, depending on the application conditions.

The fungicidal effect of the composition of the invention will be particularly illustrated by way of the following experimental examples.

EXPERIMENTAL EXAMPLE 1

Control Test For Damping-off Disease of Rice Plant Seedling (Caused by Trichoderma Sp.)

Soil was filled in nursery boxes of a length of 60 cm, a width of 30 cm and a depth of 3 cm and bran medium in which *Trichoderma viride* had been cultured was uniformly inoculated or distributed in the soil in an amount of 200 g per box. Then, the dust of the composition of the invention as prepared in the same manner as in formulation Example 1 was added in a predetermined amount and uniformly mixed with the soil.

Further, 0.3 l of seeds of rice plant (variety: Nihonbare) per box was stripe sowed and nursed for 3 days in the inoculated box of 35° C., followed by allowing to stand for further 3 days in a green house which was controlled at 25° C. in the day and at 20° C. in the night and then in a green house controlled at 20° C. in the day and at 15° C. in the night. Nine days after the sowing the control effect was observed. The test results are shown in Table 1 and expressed in terms of a control value which is determined as follows.

$$\text{Control Value} = \frac{\begin{array}{c}\text{percentage of healthy} \\ \text{seedling in treated} \\ \text{plots}\end{array} - \begin{array}{c}\text{percentage of healthy} \\ \text{seedling in un-treated} \\ \text{plots}\end{array}}{\text{percentage of healthy seedling in treated plots}} \times 100$$

$$\text{Percentage of healthy seedling} = \frac{\text{Number of healthy seedlings}}{\text{Number of total seedlings checked}} \times 100$$

Table 1

| | tested compounds | amount of effective components (g/box) | control value | phytotoxicity |
|---|---|---|---|---|
| Example of Inventions | Compound A + the hydroxyisoxazol | 1.0 + 0.24 | 85 | nil |
| | Compound A + the hydroxyisoxazol | 0.5 + 0.12 | 82 | nil |
| Reference | Compound A | 1.0 | 30 | nil |
| | " | 0.5 | 21 | nil |
| | The hydroxyisoxazol | 0.24 | 21 | nil |
| | " | 0.12 | 7 | nil |

EXPERIMENTAL EXAMPLE 2

Control Test For Damping-off Disease of Rice Plant Seedling (caused by Fusarium Sp)

Soil was filled in nursery boxes of a length of 60 cm, a width of 30 cm and a depth of 3 cm and a bran medium in which *Fusarium roseum* had been cultured was uniformly added in an amount of 200 g per box. Then, the dust of the composition of the invention as prepared in formulation Example 1 was added in a predetermined amount and uniformly mixed with the soil.

Thereafter, 0.3 l of rice plant (variety: Nihonbare) was stripe sowed and nursed in the box of 32° C. for 3 days, followed by allowing to stand for further 3 days in a green house which was controlled at 25° C. in the day and at 20° C. in the night then for 3 days in a room of 3°–5° C., and finally in a green house which was controlled at 20° C. in the day and at 15° C. in the night for nine days, and then the seedlings were observed to check.

The test results shown in Table 2 are expressed in terms of the control value. The control value was determined as in Experimental Example 1.

Table 2

|  | tested compounds | amount of effective components (g/box) | control value | phytotoxicity |
|---|---|---|---|---|
| Example of the Invention | Compound A + the hydroxyisoxazol | 0.75 + 0.12 | 97 | nil |
|  | Compound + the hydroxyisoxazol | 0.75 + 0.08 | 95 | nil |
|  | Compound A + the hydroxyisoxazol | 0.5 + 0.12 | 92 | nil |
|  | Compound + the hydroxyisoxazol | 0.5 + 0.08 | 84 | nil |
| Reference | Compound A | 1.0 | 90 | nil |
|  | " | 0.75 | 70 | nil |
|  | " | 0.5 | 30 | nil |
|  | The hydroxyisoxazol | 0.16 | 60 | nil |
|  | The hydroxyisoxazol | 0:12 | 45 | nil |
|  | The hydroxyisoxazol | 0.08 | 20 | nil |

EXPERIMENTAL EXAMPLE 3

Control Test for Damping-off Disease of Rice Plant Seedling (Caused by Rhizopus Sp.)

Soil was filled in nursery boxes of a length of 60 cm, a width of 30 cm and a depth of 3 cm and a bran medium in which Rhizopus chinesis had been cultured was uniformly inoculated in an amount of 500 g/box. Then, Experimental Example 1 was repeated with the results shown in Table 3 below.

Table 3

|  | tested compounds | amount of effective components (g/box) | control value | phytotoxicity |
|---|---|---|---|---|
| Example of the Invention | Compound A + the hydroxyisooxazol | 0.6 + 0.24 | 94 | nil |
|  | Compound A + the hydroxyisooxazol | 0.6 + 0.16 | 86 | nil |
| Reference | Compound A | 1.0 | 98 | nil |
|  | " | 0.6 | 75 | nil |
|  | The hydroxyisoxazol | 0.24 | 0 | nil |

Table 3-continued

|  | tested compounds | amount of effective components (g/box) | control value | phytotoxicity |
|---|---|---|---|---|
|  | The hydroxyisoxazol | 0.16 | 0 | nil |

EXPERIMENTAL EXAMPLE 4

Control Test for Phytophthora rot of Cucumber

Field soil was filled in pots with a diameter of 12 cm and then 5 g of infested soil in which *Phytophthora melonis* had been cultured was uniformly inoculated on the soil surface in each pot. The dust of the composition of the invention as prepared in formulation Example 1 was added in a predetermined amount and uniformly mixed with the soil.

Then seeds of cucumber (variety: Ōyashima) were sowed in each pot. The disease attack was observed by nursing the seeds in a green hourse.

20 days after the sowing, the seedlings were observed to determine the percentage of healthy seedling.

Percentage of healthy seedling = 
$$\frac{\text{Number of healthy seedlings in each treated plot}}{\text{Number of germination in un-treated, un-inoculated plot}} \times 100$$

The test results are shown in Talbe 4.

Table 4

|  | tested compounds | amount of effective components (g/pot) | Percentage of healthy seedling (%) | phytotoxicity |
|---|---|---|---|---|
| Reference | Compound A | 0.02 | 100 | nil |
|  | " | 0.01 | 65 |  |
|  | The hydroxyisoxazol | 0.01 | 10 | nil |
|  | The hydroxyisoxazol | 0.005 | 5 |  |
| Example of the Invention | Compound A + the hydroxyisoxazol | 0.01 + 0.01 | 100 | nil |
|  | Compound A + the hydroxyisoxazol | 0.01 + 0.005 | 95 |  |

What is claimed is:

1. A fungicidal composition for use in agriculture and horticulture comprising a synergistic fungicidally effective amount of 4-methylsulfonyloxyphenyl-N-methylthiolcarbamate and 3-hydroxy-5-isoxazol in a weight ratio of 1:10–10:1 and an adjuvant therefor.

2. The fungicidal composition according to claim 1, wherein the content of the effective components in said composition is in the range of 0.5 to 95% on the weight basis.

3. The fungicidal composition according to claim 1, wherein the ratio by weight of 4-methylsulfonyloxyphenyl-N-methylthiolcarbamate to 3-hydroxy-5-methylisoxazol is in the range of 1:1–6:1.

4. A method for preventing soil borne plant diseases caused by fungi which comprises treating fungi-containing soil with an effective synergistic amount of a mixture of 4-methylsulfonyoxyphenyl-N-methylthiolcarbamate and 3-hydroxy-5-methylisoxazol in a weight ratio of 1:10–10:1.

5. The method according to claim 4, wherein the ratio by weight of 4-methylsulfonyloxyphenyl-N-methylthiolcarbamate to 3-hydroxy-5-methylisoxazol is in the range of 1:1–6:1.

* * * * *